US009770558B2

(12) United States Patent
Burnell et al.

(10) Patent No.: US 9,770,558 B2
(45) Date of Patent: Sep. 26, 2017

(54) AUTO-INJECTION DEVICE WITH NEEDLE PROTECTING CAP HAVING OUTER AND INNER SLEEVES

(75) Inventors: Rosie L. Burnell, Cambridge (GB); David M. Johnston, Robbinsville, NJ (US)

(73) Assignee: Cilag gmBh International, Landis & Gyrstrasse (CH)

( * ) Notice: Subject to any disclaimer, the term of this patent is extended or adjusted under 35 U.S.C. 154(b) by 1105 days.

(21) Appl. No.: 10/578,807

(22) PCT Filed: Sep. 27, 2005

(86) PCT No.: PCT/GB2005/003725
§ 371 (c)(1),
(2), (4) Date: Nov. 11, 2008

(87) PCT Pub. No.: WO2007/036676
PCT Pub. Date: Apr. 5, 2007

(65) Prior Publication Data
US 2011/0098656 A1    Apr. 28, 2011

(51) Int. Cl.
*A61M 5/20*    (2006.01)
*A61M 5/32*    (2006.01)
*A61M 5/31*    (2006.01)

(52) U.S. Cl.
CPC ........ *A61M 5/2033* (2013.01); *A61M 5/3202* (2013.01); *A61M 5/3204* (2013.01);
(Continued)

(58) Field of Classification Search
CPC .............. A61M 5/2033; A61M 5/1454; A61M 2005/206; A61M 5/3202; A61M 5/3204;
(Continued)

(56) References Cited

U.S. PATENT DOCUMENTS 1,845,036 A    2/1932    Busher
2,019,382 A    10/1935    Aronson
(Continued)

FOREIGN PATENT DOCUMENTS

CH    518102 A    1/1972
CN    2059579 U    7/1990
(Continued)

OTHER PUBLICATIONS

International Search Report dated Sep. 5, 2005; International Application No. PCT/GB2005/002117.
(Continued)

*Primary Examiner* — Imani Hayman
*Assistant Examiner* — Matthew A Engel

(57) ABSTRACT

An injection device is described having a housing that receives a syringe having a boot that covers its needle. The syringe is biased by a return spring from an extended position to a retracted position. A drive spring advances the syringe from its retracted position to its extended position. A return spring restores the syringe to its refracted position. A releasable locking mechanism retains the syringe in its refracted position. A sleeve can be depressed to release the locking mechanism. A cap covers the sleeve, thus preventing the locking mechanism from being released. When the cap is removed, it takes the boot with it and no longer prevents the locking mechanism from being released. Then, the locking mechanism can be released and the injection cycle begun.

17 Claims, 6 Drawing Sheets

(52) U.S. Cl.
CPC ....... *A61M 5/326* (2013.01); *A61M 2005/206* (2013.01); *A61M 2005/208* (2013.01); *A61M 2005/2013* (2013.01); *A61M 2005/312* (2013.01); *A61M 2005/3109* (2013.01); *A61M 2005/3215* (2013.01)

(58) Field of Classification Search
CPC .......... A61M 5/326; A61M 2005/3215; A61M 2005/208; A61M 2005/312
USPC .......................... 604/134–136, 192, 198, 130
See application file for complete search history.

(56) References Cited

U.S. PATENT DOCUMENTS

| | | | |
|---|---|---|---|
| 2,147,616 A | | 2/1939 | Chaput |
| 2,295,849 A | | 9/1942 | Kayden |
| 2,531,267 A | | 11/1950 | Harisch |
| 2,752,918 A | * | 7/1956 | Uytenbogaar ................ 604/136 |
| 2,764,977 A | | 10/1956 | Ferguson |
| 2,828,742 A | | 4/1958 | Ashkenaz |
| 2,854,975 A | | 10/1958 | Cohen |
| 3,076,455 A | | 2/1963 | McConnaughey et al. |
| 3,131,692 A | | 5/1964 | Love |
| 3,320,955 A | * | 5/1967 | Sarnoff ........................ 604/138 |
| 3,329,146 A | | 7/1967 | Waldman |
| 3,543,603 A | | 12/1970 | Gley |
| 3,656,472 A | | 4/1972 | Moura |
| 3,702,608 A | | 11/1972 | Tibbs |
| 3,742,948 A | | 7/1973 | Post et al. |
| 3,797,488 A | | 3/1974 | Hurschman et al. |
| 3,797,489 A | | 3/1974 | Sarnoff |
| 3,880,163 A | * | 4/1975 | Ritterskamp ................ 604/136 |
| 3,976,069 A | | 8/1976 | Ong |
| 4,165,739 A | | 8/1979 | Doherty et al. |
| 4,180,070 A | | 12/1979 | Genese |
| 4,185,628 A | | 1/1980 | Kopfer |
| 4,194,505 A | | 3/1980 | Schmitz |
| 4,222,380 A | | 9/1980 | Terayama |
| 4,231,368 A | | 11/1980 | Becker |
| 4,236,516 A | | 12/1980 | Nilson |
| 4,237,882 A | | 12/1980 | Wickham |
| 4,299,238 A | | 11/1981 | Baidwan et al. |
| 4,333,459 A | | 6/1982 | Becker |
| 4,378,015 A | | 3/1983 | Wardlaw |
| 4,394,863 A | | 7/1983 | Bartner |
| 4,403,989 A | | 9/1983 | Christensen et al. |
| 4,407,283 A | | 10/1983 | Reynolds |
| 4,425,120 A | | 1/1984 | Sampson et al. |
| 4,430,082 A | | 2/1984 | Schwabacher |
| 4,521,237 A | | 6/1985 | Logothetis |
| 4,561,856 A | | 12/1985 | Cochran et al. |
| 4,627,835 A | * | 12/1986 | Fenton, Jr. ...................... 604/67 |
| 4,636,201 A | | 1/1987 | Ambrose et al. |
| 4,639,250 A | | 1/1987 | Rycroft |
| 4,642,099 A | | 2/1987 | Phillips et al. |
| 4,676,530 A | | 6/1987 | Nordgren et al. |
| 4,717,383 A | | 1/1988 | Phillips et al. |
| 4,744,786 A | | 5/1988 | Hooven et al. |
| 4,787,891 A | | 11/1988 | Levin et al. |
| 4,874,383 A | | 10/1989 | McNaughton |
| 4,874,384 A | | 10/1989 | Nunez |
| 4,929,232 A | | 5/1990 | Sweeney et al. |
| 4,969,870 A | | 11/1990 | Kramer et al. |
| 4,988,339 A | | 1/1991 | Vadher |
| 5,009,646 A | | 4/1991 | Sudo et al. |
| 5,026,349 A | | 6/1991 | Schmitz et al. |
| 5,057,079 A | | 10/1991 | Tiemann et al. |
| 5,092,842 A | | 3/1992 | Bechtold et al. |
| 5,098,400 A | | 3/1992 | Crouse et al. |
| 5,112,119 A | | 5/1992 | Cooke et al. |
| 5,114,406 A | | 5/1992 | Gabriel et al. |
| 5,122,119 A | | 6/1992 | Lucas |
| 5,137,516 A | | 8/1992 | Rand et al. |
| 5,141,496 A | | 8/1992 | Dalto et al. |
| 5,147,325 A | | 9/1992 | Mitchell et al. |
| 5,156,599 A | | 10/1992 | Ranford et al. |
| 5,176,643 A | | 1/1993 | Kramer et al. |
| 5,188,613 A | * | 2/1993 | Shaw .................. A61M 5/3234 604/111 |
| 5,190,526 A | | 3/1993 | Murray et al. |
| 5,242,400 A | * | 9/1993 | Blake, III ............. A61M 5/322 604/110 |
| 5,242,416 A | | 9/1993 | Hutson |
| 5,250,026 A | | 10/1993 | Ehrlich et al. |
| 5,250,037 A | | 10/1993 | Bitdinger |
| 5,263,933 A | | 11/1993 | Novacek et al. |
| 5,267,963 A | | 12/1993 | Bachynsky |
| 5,271,744 A | | 12/1993 | Kramer et al. |
| 5,295,965 A | | 3/1994 | Wilmot |
| 5,300,030 A | | 4/1994 | Crossman et al. |
| 5,312,364 A | | 5/1994 | Jacobs |
| 5,330,081 A | | 7/1994 | Davenport |
| 5,330,430 A | | 7/1994 | Sullivan |
| 5,356,395 A | | 10/1994 | Chen |
| 5,358,489 A | | 10/1994 | Wyrick |
| 5,364,369 A | * | 11/1994 | Reynolds ...................... 604/187 |
| 5,368,577 A | | 11/1994 | Teoh et al. |
| 5,372,586 A | | 12/1994 | Haber et al. |
| 5,385,551 A | * | 1/1995 | Shaw .................. A61M 5/3234 604/110 |
| 5,391,151 A | | 2/1995 | Wilmot |
| 5,405,362 A | | 4/1995 | Kramer et al. |
| 5,411,488 A | | 5/1995 | Pagay et al. |
| 5,425,715 A | | 6/1995 | Dalling et al. |
| 5,451,210 A | | 9/1995 | Kramer et al. |
| 5,478,316 A | * | 12/1995 | Bitdinger et al. ............. 604/135 |
| 5,480,387 A | | 1/1996 | Gabriel et al. |
| 5,487,732 A | | 1/1996 | Jeffrey |
| 5,489,256 A | | 2/1996 | Adair |
| 5,503,627 A | * | 4/1996 | McKinnon et al. ............. 604/72 |
| 5,514,097 A | | 5/1996 | Knauer |
| 5,520,653 A | | 5/1996 | Reilly et al. |
| 5,540,660 A | | 7/1996 | Jenson et al. |
| 5,540,666 A | | 7/1996 | Barta et al. |
| 5,540,709 A | | 7/1996 | Ramel et al. |
| 5,567,160 A | | 10/1996 | Massino |
| 5,569,191 A | | 10/1996 | Meyer |
| 5,569,192 A | | 10/1996 | van der Wal |
| 5,575,777 A | | 11/1996 | Cover et al. |
| 5,599,302 A | | 2/1997 | Lilley et al. |
| 5,599,309 A | * | 2/1997 | Marshall et al. .............. 604/136 |
| 5,607,395 A | | 3/1997 | Ragsdale et al. |
| 5,609,577 A | | 3/1997 | Haber et al. |
| 5,609,584 A | | 3/1997 | Gettig et al. |
| 5,611,785 A | | 3/1997 | Mito et al. |
| 5,637,094 A | | 6/1997 | Stewart, Jr. et al. |
| 5,645,536 A | | 7/1997 | Whisson |
| 5,647,845 A | | 7/1997 | Haber et al. |
| 5,649,912 A | | 7/1997 | Peterson |
| 5,658,259 A | | 8/1997 | Pearson et al. |
| 5,665,071 A | | 9/1997 | Wyrick |
| 5,681,291 A | | 10/1997 | Galli |
| 5,697,908 A | | 12/1997 | Imbert |
| 5,702,367 A | | 12/1997 | Cover et al. |
| 5,704,911 A | | 1/1998 | Parsons et al. |
| 5,709,662 A | * | 1/1998 | Olive et al. .................... 604/135 |
| 5,713,866 A | | 2/1998 | Wilmot |
| 5,748,316 A | | 5/1998 | Wakabayashi et al. |
| 5,779,668 A | | 7/1998 | Grabenkort |
| 5,779,677 A | | 7/1998 | Frezza |
| 5,807,334 A | | 9/1998 | Hodosh et al. |
| 5,817,058 A | | 10/1998 | Shaw |
| 5,827,262 A | | 10/1998 | Neftel et al. |
| 5,843,036 A | | 12/1998 | Olive et al. |
| 5,855,839 A | | 1/1999 | Brunel |
| 5,865,795 A | | 2/1999 | Schiff et al. |
| 5,865,804 A | | 2/1999 | Bachynsky |
| 5,868,711 A | | 2/1999 | Kramer et al. |
| 5,879,327 A | | 3/1999 | Moreau DeFarges et al. |
| 5,913,843 A | | 6/1999 | Jentzen |
| 5,928,205 A | | 7/1999 | Marshall |
| 5,954,738 A | | 9/1999 | LeVaughn et al. |
| 5,957,897 A | | 9/1999 | Jeffrey |
| 5,960,797 A | | 10/1999 | Kramer et al. |

(56) References Cited

U.S. PATENT DOCUMENTS

| | | | |
|---|---|---|---|
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A * | 12/2000 | Crossman et al. ............ 604/157 |
| 6,159,184 A | 12/2000 | Perez et al. |
| 6,162,199 A | 12/2000 | Geringer |
| 6,171,276 B1 | 1/2001 | Markus et al. |
| 6,179,812 B1 | 1/2001 | Botich et al. |
| 6,186,980 B1 * | 2/2001 | Brunel .......................... 604/110 |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,209,738 B1 | 4/2001 | Jansen et al. |
| 6,221,044 B1 | 4/2001 | Greco |
| 6,228,055 B1 | 5/2001 | Foerster et al. |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydlon et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B2 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landua |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,817,987 B2 | 11/2004 | Vetter et al. |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,939,330 B1 | 9/2005 | McConnell et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,409,138 B2 | 4/2013 | James et al. |
| 8,409,141 B2 | 4/2013 | Johansen et al. |
| 8,491,530 B2 | 7/2013 | Maritan |
| 8,696,628 B2 | 4/2014 | Grunhut |
| 8,932,264 B2 | 1/2015 | DeSalvo |
| 9,248,245 B2 * | 2/2016 | Ekman ................ A61M 5/2033 |
| 9,314,574 B2 | 4/2016 | Roberts et al. |
| 2001/0005781 A1 | 6/2001 | Bergens et al. |

(56) References Cited

U.S. PATENT DOCUMENTS

| | | |
|---|---|---|
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sahrpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178630 A1 | 8/2006 | Bostrom et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1* | 2/2010 | Drake et al. .................. 604/135 |
| 2010/0063444 A1 | 3/2010 | Wikner |
| 2011/0092954 A1* | 4/2011 | Jennings ..................... 604/506 |
| 2011/0098647 A1* | 4/2011 | Jennings ..................... 604/154 |
| 2011/0098655 A1 | 4/2011 | Jennings et al. |
| 2011/0130743 A1* | 6/2011 | Jennings et al. ............ 604/506 |
| 2011/0282278 A1 | 11/2011 | Stamp et al. |
| 2012/0232491 A1 | 9/2012 | Jennings |
| 2012/0283698 A1* | 11/2012 | Millerd ............... A61M 5/2429 |
| | | 604/506 |
| 2012/0323177 A1 | 12/2012 | Adams et al. |
| 2013/0060232 A1* | 3/2013 | Adlon ................. A61M 5/2066 |
| | | 604/506 |
| 2013/0096512 A1 | 4/2013 | Ekman et al. |

(56) References Cited

U.S. PATENT DOCUMENTS

| | | | |
|---|---|---|---|
| 2013/0150801 A1* | 6/2013 | Ekman | A61M 5/2033 604/198 |
| 2013/0267898 A1 | 10/2013 | Hourmand et al. | |
| 2013/0310759 A1* | 11/2013 | Hourmand | A61M 5/2033 604/198 |
| 2013/0317446 A1 | 11/2013 | Hourmand et al. | |
| 2013/0331794 A1 | 12/2013 | Ekman et al. | |
| 2013/0338601 A1 | 12/2013 | Cowe | |
| 2013/0345643 A1 | 12/2013 | Hourmand et al. | |
| 2014/0221974 A1* | 8/2014 | Bechmann | A61M 5/2033 604/506 |
| 2014/0257185 A1* | 9/2014 | Bechmann | A61M 5/2033 604/135 |
| 2014/0257193 A1 | 9/2014 | Bostrom et al. | |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0338806 A2 | 10/1989 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |
| EP | 2760507 B1 | 4/2016 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 A | 6/1978 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 59-115053 A | 7/1984 |
| JP | 2-185261 A | 7/1990 |
| JP | 2-502971 T | 9/1990 |
| JP | H 02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |

(56) References Cited

FOREIGN PATENT DOCUMENTS

| | | |
|---|---|---|
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2007-207611 A | 8/2007 |
| JP | 2008-284177 A | 11/2008 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/08725 | 11/1988 |
| WO | WO 88/10129 A1 | 12/1988 |
| WO | WO 8810129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 A2 | 2/2003 |
| WO | WO 03/015846 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/066152 A2 | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 2010/023303 A1 | 3/2010 |
| WO | WO 2012/000835 A1 | 1/2012 |

OTHER PUBLICATIONS

International Search Report dated May 30, 2006; International Application No. PCT/GB2005/003725.

(56) References Cited

OTHER PUBLICATIONS

International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11170040.
European Search Report dated Aug. 3, 2011; Application No. 11163779.9.
Singapore Search Report dated Mar. 15, 2012; Application No. SG 201007017-5.
European Search Report dated Jul. 20, 2011; Application No. 11163762.5.
Australian Search Report dated Feb. 26, 2008; Application No. SG 200608071-7.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Jun. 16, 2011; Application No. 11160134.0.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug. 4, 2011; Application No. 11169691.0.
Great Britain Search Report dated Sep. 29, 2006; Application No. GB0610856.7.
Great Britain Search Report dated Sep. 19, 2006; Application No. GB0610861.7.
European Search Report dated Oct. 15, 2013; Application No. 12182553.3.
Great Britain Search Report dated Dec. 9, 2013; Application No. GB1310394.0.

(56) References Cited

OTHER PUBLICATIONS

International Search Report dated Sep. 8, 2014; International Application No. PCT/EP2014/062163.
Great Britain Search Report dated Dec. 8, 2013; Application No. GB1310389.0.
International Search Report dated Sep. 8, 2014; International Application No. PCT/EP2014/062166.
Great Britain Search Report dated Dec. 9, 2013; Application No. GB1310402.1.
International Search Report dated Sep. 17, 2014; International Application No. PCT/EP2014/062167.
Great Britain Search Report dated Dec. 9, 2013; Application No. GB1310392.4.
International Search Report dated Sep. 9, 2014; International Application No. PCT/EP2014/062168.
Great Britain Search Report dated Dec. 10, 2013; Application No. GB1310393.2.
International Search Report dated Sep. 8, 2014; International Application No. PCT/EP2014/062162.
Great Britain Search Report dated Dec. 10, 2013; Application No. GB1310372.6.
International Search Report dated Sep. 16, 2014; International Application No. PCT/EP2014/062160.
International Search Report dated Jan. 29, 2015; International Application No. PCT/EP2014/062167.
European Search Report dated Apr. 28, 2015; Application No. 15153304.9.
International Preliminary Report dated Dec. 15, 2015; International Application No. PCT/EP2014/062163.
International Preliminary Report dated Dec. 15, 2015; International Application No. PCT/EP2014/062166.

\* cited by examiner

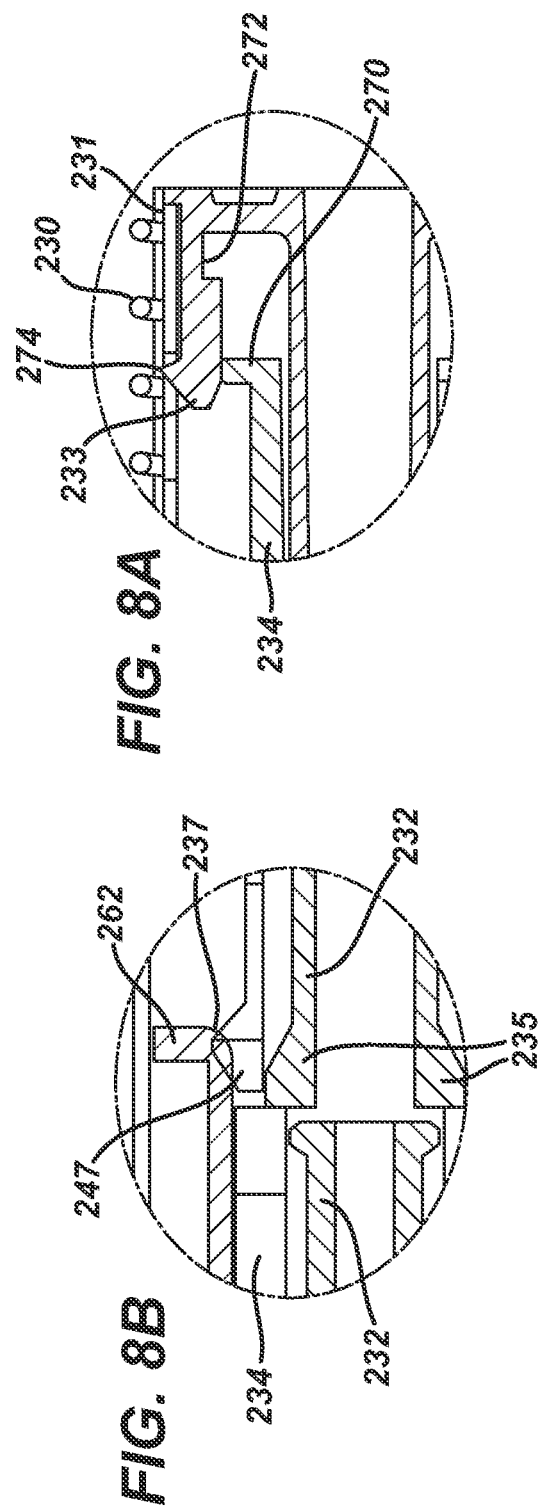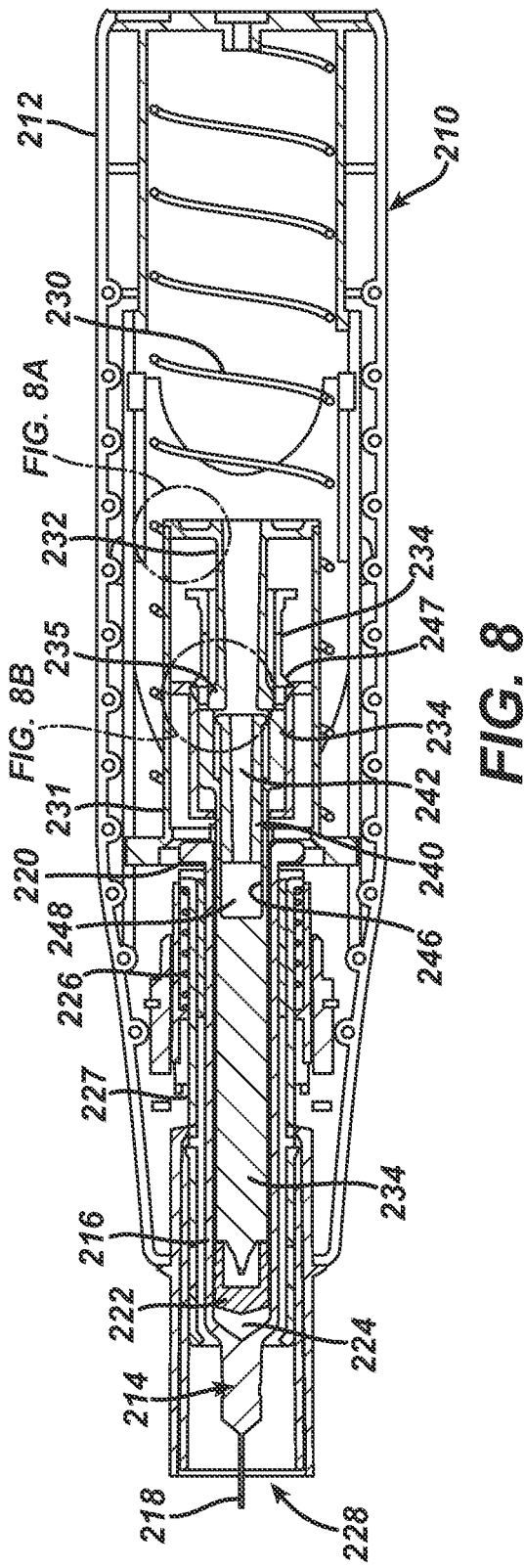

AUTO-INJECTION DEVICE WITH NEEDLE PROTECTING CAP HAVING OUTER AND INNER SLEEVES

BACKGROUND TECHNOLOGY

The present invention relates to an injection device of the type that receives a syringe, extends it, discharges its contents and then retracts it automatically. Devices of this general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

Generally, the return spring is relatively weak, since its restoring force must be overcome by the drive spring, even while the drive spring is doing work on the various components of the injector device and the syringe during an injection cycle. This may give rise to a problem when the injection device is used with sealed hypodermic syringes, which typically have a hermetically sealed cover or "boot" that covers the hypodermic needle and maintains the sterility of the syringe contents. Naturally, it is necessary to maintain the sterility of the syringe contents up to the point of administration, which devices that are designed to be disposable, as many will be, means that the boot must be removed with the syringe inside the injection device.

Typically, the action required to remove the boot from the syringe is simply to pull the boot away from the syringe, which requires a force in excess of 20 N. This is significantly greater than the restoring force of the return spring, so the syringe will be pulled out of the injection device as the boot is removed and, when the boot comes away, it will snap back into place. This is not the best way to handle the syringe. The shock could damage it, the needle could be damaged and there may be problems re-engaging the syringe with those components of the injection device designed to act upon it. Even in cases where there is no return spring, for example where the syringe is held in place by friction with components of the injection device, the problem will still arise of relocating the syringe onto those components of the injection device designed to act upon it.

SUMMARY OF THE INVENTION

The injection devices of the present invention are designed to deal with these problems.

An injection device according to a first aspect of the invention comprises:
  a housing adapted to receive a syringe having a discharge nozzle and having a boot that covers its discharge nozzle, so that the syringe is movable between a retracted position in which the discharge nozzle is contained within the housing and an extended position in which the discharge nozzle extends from the housing through an exit aperture;
  a releasable locking mechanism that retains the syringe in its retracted position; and
  a housing closure member that can occupy a first position, in which it locates on the housing and prevents the locking mechanism from being released, and a second position, in which it does not prevent the locking mechanism from being released, the first position of the housing closure member being one in which it engages the boot, so that movement of the housing closure member to its second position results in removal of the boot from the syringe.

When the housing closure member is in its first position, it not only locates on the housing and engages the boot, but it also prevents the locking mechanism from being released. Thus, the syringe is locked into its retracted position and cannot be driven forwards. When the housing closure member is moved, it takes the boot with it, during which process the locking mechanism still prevents the syringe from moving. Afterwards, the locking mechanism can be released as required, allowing the syringe to be driven forwards when the device is used. Therefore, the syringe can move forwards only once the boot has been removed, not during its removal.

Preferably the device further comprises:
  an actuator, and
  a drive that is acted upon by the actuator and in turn acts upon the syringe to advance it from its retracted position to its extended position and discharge its contents through the discharge nozzle.

Preferably, when the housing closure member is in its first position, it closes the exit aperture to the discharge nozzle. For convenience, the closure member may be removable. In other words, the first position of the housing closure member is one in which it locates on the housing and the second position is one in which it does not. For example, the housing closure member could be a cap that locates onto the housing by means of a thread.

As discussed above, it is conventional for the housing to include means for biasing the syringe from its extended position to its retracted position, In such a case, a return mechanism is preferably present, activated when the drive has reached a nominal return position, to release the syringe from the action of the actuator, whereupon the biasing means restores the syringe to its retracted position.

The device may include a release mechanism operable to release the locking mechanism, thus allowing the syringe to be advanced by the actuator from its retracted position to its extended position. In that case, the first position of the housing closure member is one in which it prevents the release mechanism from being operated. For example, the release mechanism may be a primary member movable between locking and releasing positions, the first position of the housing closure member being one in which it covers the primary member.

A particularly effective arrangement is one in which the locking position of the primary member is one in which it projects from the exit aperture and the releasing position is one in which it does not project from the exit aperture or projects from it to a lesser extent. This means that the primary member may be moved from its locking position to its releasing position by bringing the end of the injection device into contact with the skin at the injection site. Apart from anything else, this ensures that the injection device is optimally positioned relative to the injection site before the injection cycle can begin. A primary member in the form of a sleeve allows a relatively large area to contact the skin and allows the discharge nozzle of the syringe to be advanced and retracted within it. In the case of a hypodermic syringe, the sleeve will shroud the needle from view, which is a good idea for the squeamish, particularly those who have to administer to themselves.

A simple form of locking mechanism comprises a latch member that is located within the housing and is biased into a position in which it engages a locking surface, the release mechanism acting to move it from that position into a position in which it no longer engages the locking surface.

When combined with the movable primary member as just described, the following arrangement can be obtained. The primary member includes a latch opening through which the latch member projects before it engages the locking surface, the primary member acting as a cam and the latch member as a cam follower, so that movement of the primary member from its locking position to its releasing position causes the latch member to disengage from the locking surface. The latch member may include a ramped surface against which a surface of the primary member acts to disengage it from the locking surface.

The injection device may further comprise:
a trigger movable from a rest position, in which it causes the drive to be retained in a position corresponding to the retracted position of the syringe, to an active position, in which it no longer causes the drive to be so retained, thus allowing it to be advanced by the actuator and in turn to advance the syringe from its retracted position to its extended position and discharge its contents through the discharge nozzle; and
an interlock member movable between a locking position, at which it prevents movement of the trigger from its rest position to its active position, and a releasing position, at which it allows movement of the trigger from its rest position to its active position, the trigger thereafter being retained in its active position.

Such a device provides a visual indication that it is either ready to use or has been used. If it is ready for use, the trigger will be in its rest position. If it has been used, the trigger will be in its active position. These positions can be discriminated by the user. Moreover, the device incorporates the mechanism for achieving this result into a safety interlock mechanism, in the interests of simplicity. The trigger may comprise a locking member that, in the rest position of the trigger, engages a locking surface of the drive and, in the active position, does not.

The interlock member may comprises a primary member, the locking position of the interlock member being one in which the primary member projects from the exit aperture and the releasing position being one in which the primary member does not project from the exit aperture or projects from it to a lesser extent. This means that the interlock member may be moved from its locking position to its releasing position by bringing the end of the injection device into contact with the skin at the injection site. Apart from anything else, this ensures that the injection device is optimally positioned relative to the injection site before the injection cycle can begin. A primary member in the form of a sleeve allows a relatively large area to contact the skin and allows the discharge nozzle of the syringe to be advanced and retracted within it. In the case of a hypodermic syringe, the sleeve will shroud the needle from view, which is a good idea for the squeamish, particularly those who have to administer to themselves.

The locking of the trigger in its rest position may be achieved as follows. The trigger and the interlock member include a projection and an aperture, the projection being in register with the aperture when the interlock member is in its releasing position, but not otherwise. This allows the trigger to move from its rest position to its active position by movement of the projection into the aperture. The projection may be on the trigger and the aperture is in the interlock member.

The retention of the trigger in its active position may be achieved as follows. The trigger and another component of the device include a latching projection and a corresponding latching surface against which the latching projection latches when the trigger is in its active position. The latching projection may be on the trigger. This other component of the device is preferably the interlock member.

BRIEF DESCRIPTION OF THE DRAWINGS

The invention will now be described by way of example with reference to the accompanying drawings, in which:
FIG. 8 shows in section a preferred injection device.

DETAILED DESCRIPTION

Figure 1:
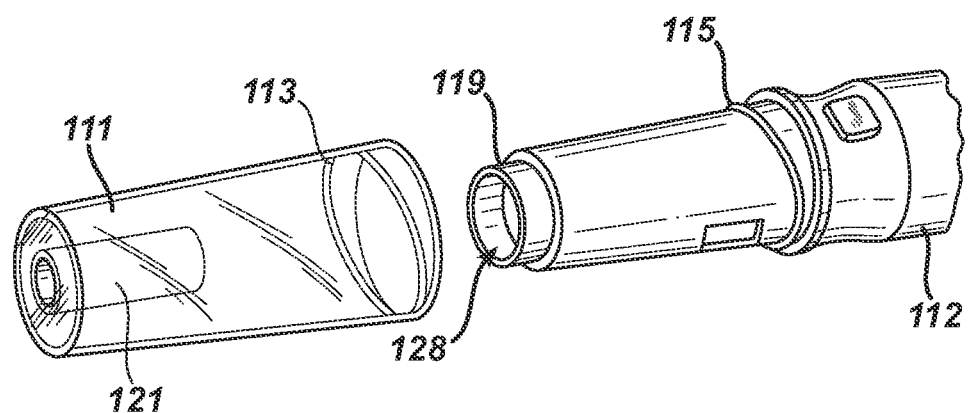
FIG. 1 shows the end of in injection device before a cap is affixed to it.
Figure 2:
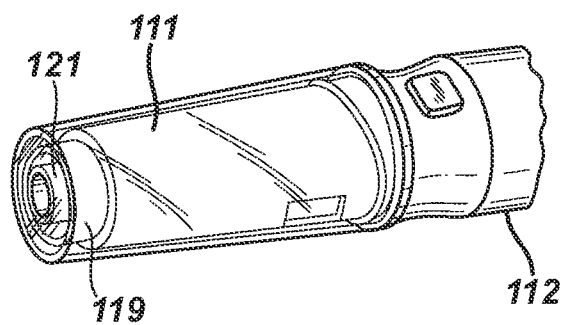
FIG. 2 shows it once the cap has been affixed.

FIG. 1 shows the end of an injection device housing 112 and a cap 111. Other parts of the device will be described in greater detail below, but it will be seen that the cap 111 includes a thread 113 that cooperates with a corresponding thread 115 on the end of the housing. The end of the housing 112 has an exit aperture 128, from which the end of a sleeve 119 can be seen to emerge. The cap 111 has a central boss 121 that fits within the sleeve 119 when the cap 111 is installed on the housing 112, as can be seen in FIG. 2.

Figure 3:
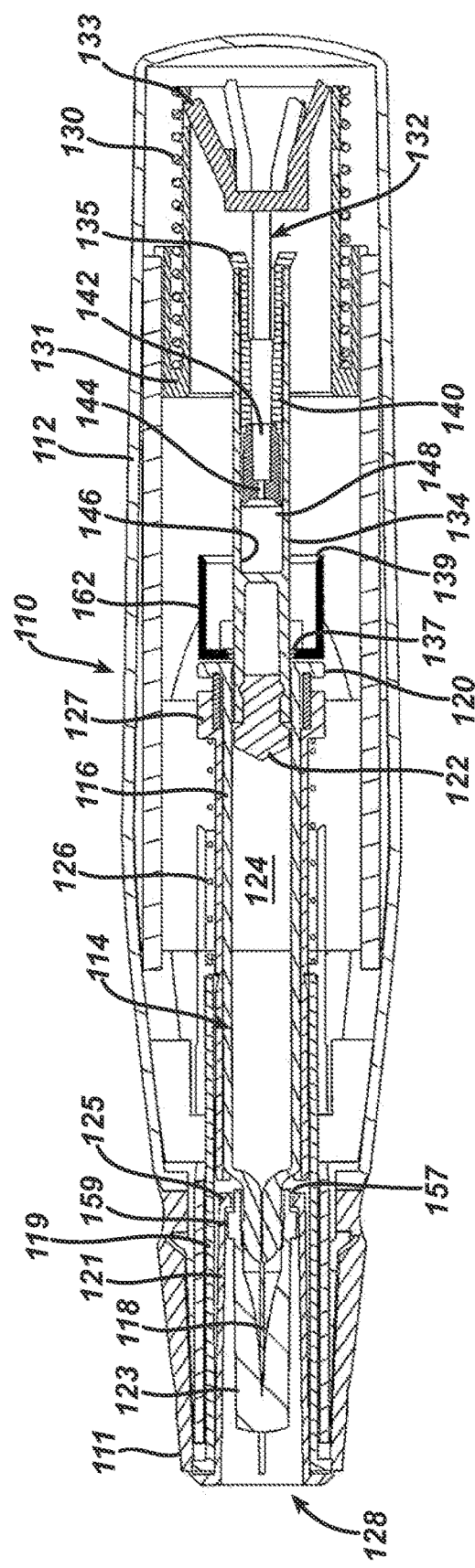
FIG. 3 shows in section a device with the cap affixed.

FIG. 3 shows an injection device 110 in more detail. The housing 112 contains a hypodermic syringe 114 of conventional type, including a syringe body 116 terminating at one end in a hypodermic needle 118 and at the other in a flange 120. The conventional plunger that would normally be used to discharge the contents of the syringe 114 manually has been removed and replaced with a drive element 134 that terminates in a bung 122. The bung 122 constrains a drug 124 to be administered within the syringe body 116. Whilst the syringe illustrated is of hypodermic type, this need not necessarily be so. Transcutaneous or ballistic dermal and subcutaneous syringes may also be used with the injection device of the present invention. As illustrated, the housing includes a return spring 126 that biases the syringe 114 from an extended position in which the needle 118 extends from an aperture 128 in the housing 112 to a retracted position in which the discharge nozzle 118 is contained within the housing 112. The return spring 126 acts on the syringe 114 via a syringe carrier 127.

At the other end of the housing is an actuator, which here takes the form of a compression drive spring 130. Drive from the drive spring 130 is transmitted via a multi-component drive to the syringe 114 to advance it from its retracted position to its extended position and discharge its contents through the needle 118. The drive accomplishes this task by acting directly on the drug 124 and the syringe 114. Hydrostatic forces acting through the drug 124 and, to a lesser extent, static friction between the bung 122 and the syringe body 116 initially ensure that they advance together, until the return spring 126 bottoms out or the syringe body 116 meets some other obstruction (not shown) that retards its motion.

The multi-component drive between the drive spring 130 and the syringe 114 consists of three principal components. A drive sleeve 131 takes drive from the drive spring 130 and transmits it to flexible latch arms 133 on a first drive element 132. This in turn transmits drive via flexible latch arms 135 to a second drive element, the drive element 134 already mentioned.

The first drive element 132 includes a hollow stem 140, the inner cavity of which forms a collection chamber 142 in communication with a vent 144 that extends from the collection chamber through the end of the stem 140. The second drive element 134 includes a blind bore 146 that is open at one end to receive the stem 140 and closed at the other. As can be seen, the bore 146 and the stem 140 defining a fluid reservoir 148, within which a damping fluid is contained.

A trigger (not shown) is provided that, when operated, serves to decouple the drive sleeve 131 from the housing 112, allowing it to move relative to the housing 112 under the influence of the drive spring 130. The operation of the device is then as follows.

Initially, the drive spring 130 moves the drive sleeve 131, the drive sleeve 131 moves the first drive element 32 and the first drive element 132 moves the second drive element 134, in each case by acting through the flexible latch arms 133, 135. The second drive element 134 moves and, by virtue of static friction and hydrostatic forces acting through the drug 124 to be administered; moves the syringe body 116 against the action of the return spring 126. The return spring 126 compresses and the hypodermic needle 118 emerges from the exit aperture 128 of the housing 112. This continues until the return spring 126 bottoms out or the syringe body 116 meets some other obstruction (not shown) that retards its motion. Because the static friction between the second drive element 134 and the syringe body 116 and the hydrostatic forces acting through the drug 124 to be administered are not sufficient to resist the full drive force developed by the drive spring 130, at this point the second drive element 134 begins to move within the syringe body 116 and the drug 124 begins to be discharged. Dynamic friction between the second drive element 134 and the syringe body 116 and hydrostatic forces acting through the drug 124 to be administered are, however, sufficient to retain the return spring 126 in its compressed state, so the hypodermic needle 118 remains extended.

Before the second chive element 134 reaches the end of its travel within the syringe body 116, so before the contents of the syringe have fully discharged, the flexible latch arms 135 linking the first and second drive elements 132, 134 reach a constriction 137 within the housing 112. The constriction 137 moves the flexible latch arms 135 inwards from the position shown to a position at which they no longer couple the first drive element 132 to the second drive element 134, aided by the bevelled surfaces on the constriction 137. Once this happens, the first drive element 132 acts no longer on the second drive element 134, allowing the first drive element 132 to move relative to the second drive element 134.

Because the damping fluid is contained within a reservoir 148 defined between the end of the first drive element 132 and the blind bore 146 in the second drive element 134, the volume of the reservoir 146 will tend to decrease as the first drive element 132 moves relative to the second drive element 134 when the former is acted upon by the drive spring 130. As the reservoir 148 collapses, damping fluid is forced through the vent 144 into the collection chamber 142. Thus, once the flexible latch arms 135 have been released, the force exerted by the drive spring 130 does work on the damping fluid, causing it to flow though the constriction formed by the vent 144, and also acts hydrostatically through the fluid and through friction between the first and second drive elements 132, 134, thence via the second drive element 134. Losses associated with the flow of the damping fluid do not attenuate the force acting on the body of the syringe to a great extent. Thus, the return spring 126 remains compressed and the hypodermic needle remains extended.

After a time, the second drive element 134 completes its travel within the syringe body 116 and can go no further. At this point, the contents of the syringe 114 are completely discharged and the force exerted by the drive spring 130 acts to retain the second drive element 134 in its terminal position and to continue to cause the damping fluid to flow though the vent 144, allowing the first drive element 132 to continue its movement.

Before the reservoir 148 of fluid is exhausted, the flexible latch arms 133 linking the drive sleeve 131 with the first drive element 132 reach another constriction 139 within the housing 112. The constriction 139 moves the flexible latch arms 133 inwards from the position shown to a position at which they no longer couple the drive sleeve 131 to the first drive element 132, aided by the bevelled surfaces on the constriction 139. Once this happens, the drive sleeve 131 acts no longer on the first drive element 132, allowing them to move relative each other. At this point, of course, the syringe 114 is released, because the forces developed by the drive spring 130 are no longer being transmitted to the syringe 114, and the only force acting on the syringe will be the return force from the return spring 126. Thus, the syringe 114 is now returned to its retracted position and the injection cycle is complete.

All this takes place, of course, only once the cap 111 has been removed from the end of the housing 112. As can be seen from FIG. 3, the end of the syringe is sealed with a boot 123. The central boss 121 of the cap that fits within the sleeve 119 when the cap 111 is installed on the housing 112, is hollow at the end and the lip 125 of the hollow end is bevelled on its leading edge 157, but not its trailing edge. Thus, as the cap 111 is installed, the leading edge 157 of the lip 125 rides over a shoulder 159 on the boot 123. However, as the cap 111 is removed, the trailing edge of the lip 125 will not ride over the shoulder 159, which means that the boot 123 is pulled off the syringe 114 as the cap 111 is removed.

Figure 4:
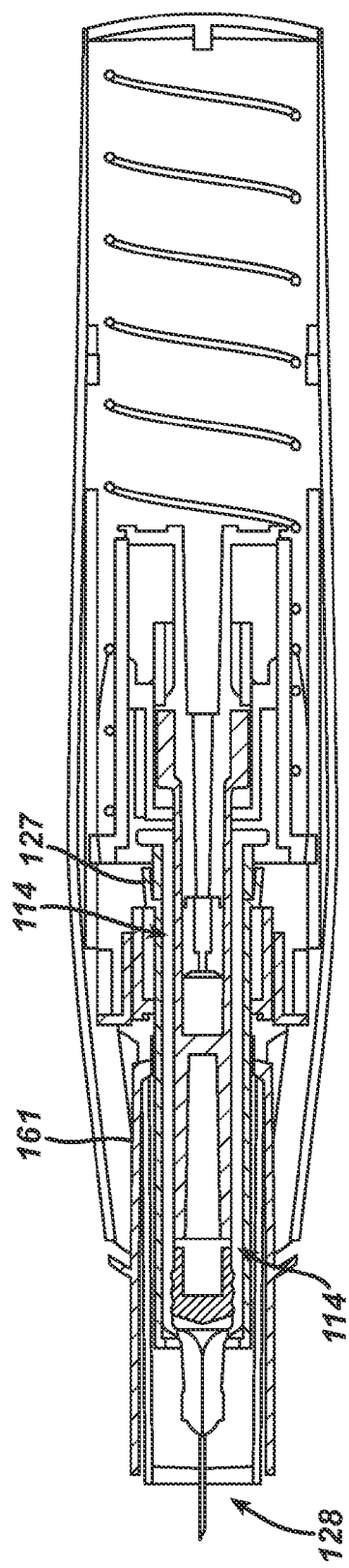
FIG. 4 shows in section a device after the cap has been removed.
Figure 5:
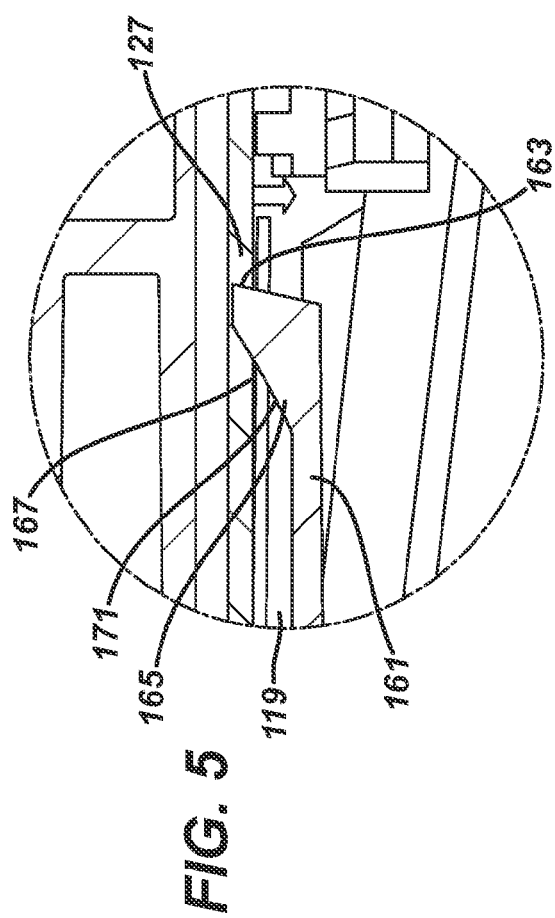
FIG. 5 is an enlarged cut-out from FIG. 4.

Meanwhile, as can best be seen in FIGS. 4 and 5, the syringe carrier 127, with respect to which the syringe 114 cannot move, is prevented from movement by a resilient latch member 161 that is located within the housing 112 and is biased into a position in which it engages a locking surface 163 of a syringe carrier 127. Before engaging the locking surface 163, the latch member 161 also extends thorough a latch opening 165 in the sleeve 119, the end of which projects from the exit aperture 128. The latch member 161 includes a ramped surface 167 against which an edge 171 of the latch opening 165 acts in the manner of a cam acting on a cam follower. Thus, movement of the sleeve 119 in a direction into the housing 112, or in other words depression of the projecting end of the sleeve, brings the edge 171 of the latch opening 165 into contact with the ramped surface 167 of the latch member 161 and further depression causes the latch member 161 to move outwards and thus to disengage from the locking surface 163. The sleeve 119 may be depressed by bringing the end of the injection device into contact with the skin at an injection site. Once the latch member 161 has disengaged from the locking surface 163, the syringe carrier 127 is free to move as required under the influence of the actuator and drive.

Figure 6:
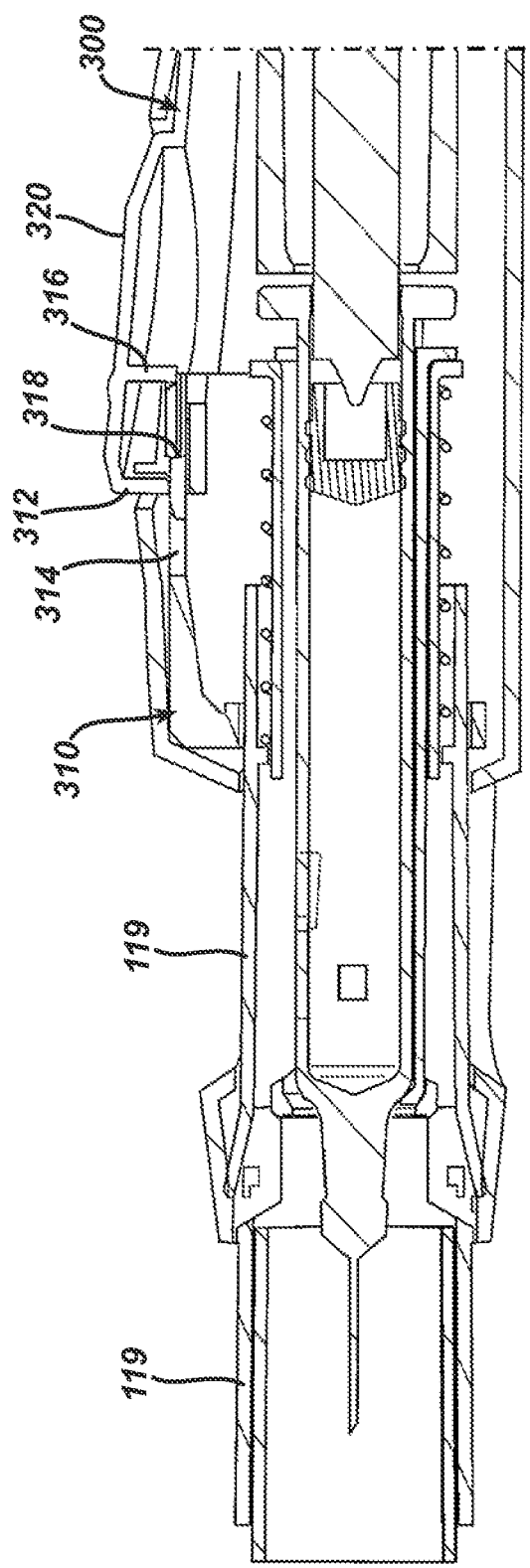
FIG. 6 shows in sectional schematic how an injection device may be further modified.
Figure 7:
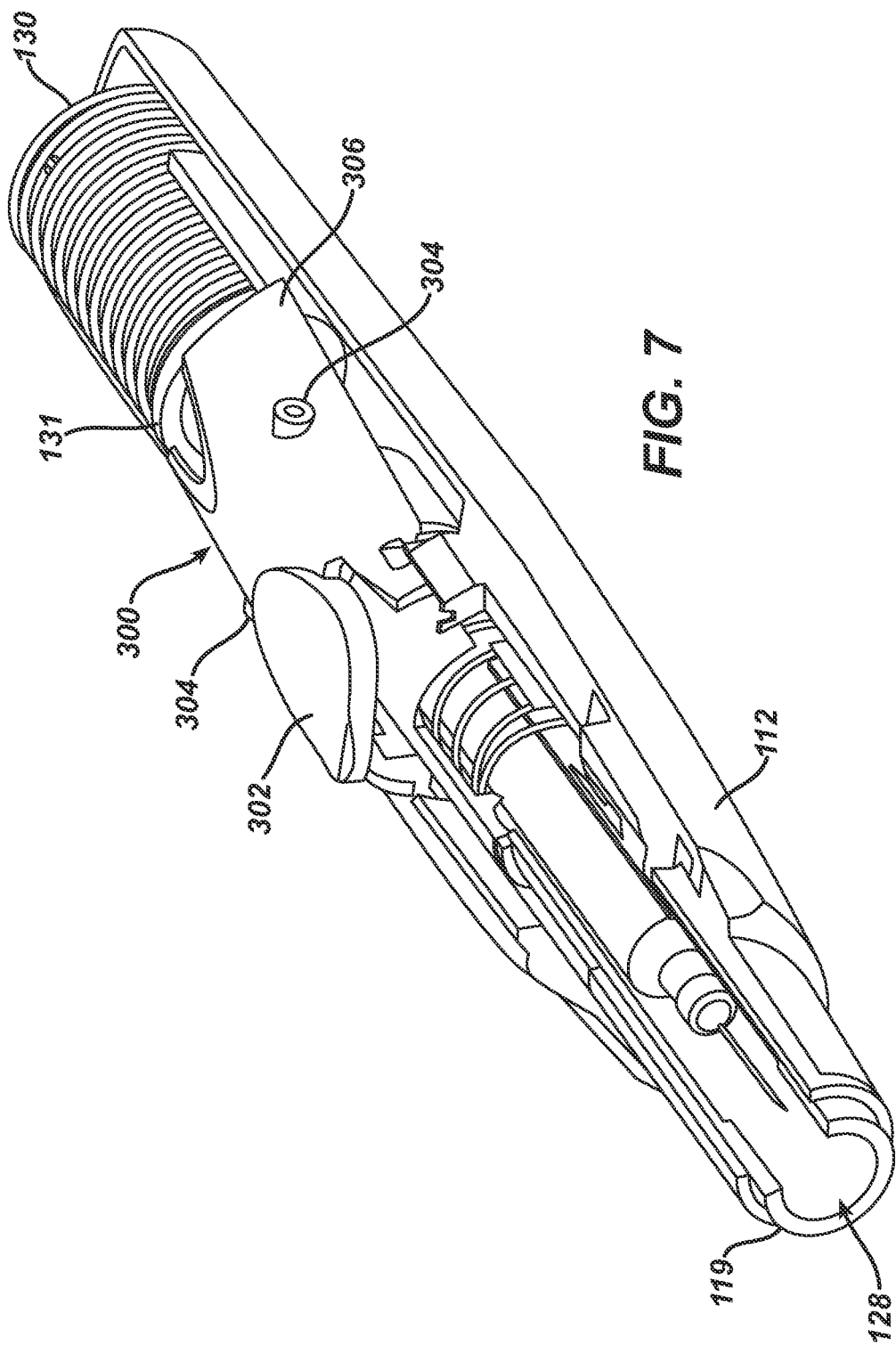
FIG. 7 is a cut-away view of such a modified injection device.

FIGS. 6 and 7 show the device may be further modified. Although FIGS. 6 and 7 differ from FIGS. 4 and 5 in some details, the principles now discussed are applicable to the device shown in FIGS. 4 and 5. As can be seen, the device includes a trigger 300 having a button 302 at one end and a pair of lugs 304 that cooperate with pins (not shown) on the inside of the housing 112 to allow the trigger to pivot about an axis through the two lugs 304. The main body portion of the trigger 300, to which both the button 302 and the lugs 304 are affixed, forms a locking member 306. In the position shown, the end of the locking member 306 remote from the button 302 engages the end of the drive sleeve 131, against which the drive spring 130 acts and which in turn acts upon the multi-component drive previously discussed. This prevents the drive sleeve 131 from moving under the influence of the drive spring 130. When the button 302 is depressed, the trigger 300 pivots about the lugs 304, which lifts the end of the locking member 306 from its engagement with the drive sleeve 131, now allowing the drive sleeve 131 to move under the influence of the drive spring 130.

FIG. 7 shows the exit aperture 128 in the end of the housing 112, from which the end of the sleeve 119 can again be seen to emerge. As is shown in FIG. 6, the sleeve 119 is coupled to a button lock 310 which moves together with the sleeve 119. The trigger includes a stop pin 312 and the button lock 310 includes an stop aperture 314 which, as shown in FIG. 6, are out of register. They can, however, be brought into register by inward movement of the sleeve 119, which results in a corresponding movement of the button lock 310. Whilst the stop pin 312 and the stop aperture 314 are out of register, the button 302 may not be depressed; once they are in register, it may. The trigger 300 also includes a flexible, barbed latching projection 316 and the button lock 310 also includes a latching surface 318 with which the latching projection 316 engages when the button is depressed. Once the latching projection 316 has latched with the latching surface 318, the trigger 300 is permanently retained with the button 302 in its depressed position.

Thus, movement of the sleeve 119 in a direction into the housing 112, or in other words depression of the projecting end of the sleeve, brings the stop pin 312 into register with the stop aperture 314, allowing the trigger button 302 to be depressed, whereupon it is retained in its depressed position by the latching projection 316 and the latching surface 318. The sleeve 119 may be depressed by bringing the end of the injection device into contact with the skin at an injection site which, apart from anything else, ensures it is properly positioned before the injection cycle begins.

The use of the sleeve 119 both the release and lock the trigger 300 and to allow the syringe carrier 127 to move, together with a boot-removing cap 111 that prevents the sleeve 119 from being depressed results in an integrated injection device of elegant design.

FIG. 8 shows a preferred injection device 210 to which the improvements described above with reference to FIGS. 6 and 7 are applied. Again, a housing 212 contains a hypodermic syringe 214. The syringe 214 is again of conventional type, including a syringe body 216 terminating at one end in a hypodermic needle 218 and at the other in a flange 220, and a rubber bung 222 that constraints a drug 224 to be administered within the syringe body 216. The conventional plunger that would normally be connected to the bung 222 and used to discharge the contents of the syringe 214 manually, has been removed and replaced with a multi-component drive element as will be described below. Whilst the syringe illustrated is again of hypodermic type, this need not necessarily be so. As illustrated, the housing includes a return spring 226 that biases the syringe 214 from an extended position in which the needle 218 extends from aperture 228 in the housing 212, to a retracted position in which the hypodermic needle 218 is contained within the housing 212. The return spring 226 acts on the syringe 214 via a sleeve 227.

At the other end of the housing is a compression drive spring 230. Drive from the drive spring 230 this transmitted via the multi-component drive to the syringe 214 to advance it from its retracted position to its extended position and discharge its contents through the needle 218. The drive accomplishes this task by acting directly on the drug 224 and the syringe 214. Hydrostatic forces acting through the drug 224 and, to a lesser extent, static friction between the bung 222 and the syringe body 216 initially ensure that they advance together, until the return spring 226 bottoms out or the syringe body 216 meets some other obstruction that retards its motion.

The multi component drive between the drive spring 230 and the syringe 214 again consists of three principal components. The drive sleeve 231 takes drive from the drive spring 230 and transmits it to flexible latch arms 233 on a first drive element 232. These elements are shown in detail "A". The first drive element 232 in turn transmits drive via flexible latch arms 235 to a second drive element 234. These elements are shown in detail "B". As before, the first drive element 232 includes a hollow stem 240, the inner cavity of which forms a collection chamber 242. The second drive element 234 includes a blind for 246 that is open at one end to receive the stem 240 and closed at the other. As can be seen, the bore 246 and the stem 240 define a fluid reservoir 248, within which a damping fluid is contained.

A trigger as described above with reference to FIGS. 6 and 7 is provided in the middle of the housing 212. The trigger, one operated, serves to decouple the drive sleeve 231 from the housing 212 allowing it to move relative to the housing 212 under the influence of the drive spring 230. The operation of the device is then as follows.

Initially, the drive spring 130 moves the drive sleeve 131, the drive sleeve 131 moves the first drive element 132 and the first drive element 132 moves the second drive element 134, in each case by acting through the flexible latch arms 133, 135. The second drive element 234 moves and, by virtue of static friction and hydrostatic forces acting through the drug 224 to be administered, moves the syringe body 216 against the action of the return spring 226. The return spring 226 compresses and the hypodermic needle 218 emerges from the exit aperture 228 of the housing 212. This continues until the return spring 226 bottoms out or the syringe body 216 meets some other obstruction that retards its motion. Because the static friction between the bung 222 and the syringe body 216 and the hydrostatic forces acting through the drug 224 to be administered are not sufficient to resist the full drive force developed by the drive spring 230, at this point the second drive element 234 begins to move within the syringe body 216 and the drug 224 begins to be discharged. Dynamic friction between the bung 222 and the syringe body 216 and hydrostatic forces acting through the drug 224 to be administered are, however, sufficient to retain the return spring 226 in its compressed state, so the hypodermic needle 218 remains extended.

Before the second drive element 234 reaches the end of its travel within the syringe body 216, so before the contents of the syringe have fully discharged, the flexible latch arms 235 linking the first and second drive elements 232, 234 reach a constriction 237. The constriction 237 is formed by a component 262 that is initially free to move relative to all other components, but that is constrained between the syringe flange 220 and additional flexible arms 247 on the second drive element 234. These additional flexible arms 247 overlie the flexible arms 235 on the first drive element 232, by means of which drive is transmitted to the second drive element 234. FIG. 3 illustrates the injection device 210 at the position where the additional flexible arms 247 are just making contact with the constriction 237 in the component 262.

The constriction 237 moves the additional flexible arms 247 inwards, aided by the bevelled surfaces on both, and the additional flexible arms 247 in turn move the flexible arms 235, by means of which drive is transmitted from the first drive element 232 to the second drive element 234, inwards from the position shown to a position at which they no longer couple the first and second drive elements together. Once this happens, the first drive element 232 acts no longer on the second drive element 234, allowing the first drive element 232 to move relative to the second drive element 234.

Because the damping fluid is contained within a reservoir 248 defined between the end of the first drive element 232 and the blind bore 246 in the second drive element 234, the volume of the reservoir 248 will tend to decrease as the first drive element 232 moves relative to the second drive element 234 when the former is acted upon by the drive spring 230. As the reservoir 248 collapses, damping fluid is forced into the collection chamber 242. Thus, once the flexible latch arms 235 have been released, the force exerted by the drive spring 230 does work on the damping fluid, causing it to flow into the collection chamber 242, and also acts hydrostatically through the fluid and through friction between the first and second drive elements 232, 234, thence via the second drive element 234. Losses associated with the flow of the damping fluid do not attenuate the force acting on the body of the syringe to a great extent. Thus, the return spring 226 remains compressed and the hypodermic needle remains extended.

After a time, the second drive element 234 completes its travel within the syringe body 216 and can go no further. At this point, the contents of the syringe 214 are completely discharged and the force exerted by the drive spring 230 acts to retain the second drive element 234 in its terminal position and to continue to cause the damping fluid to flow into the collection chamber 142, allowing the first drive element 232 to continue its movement.

A flange 270 on the rear of the second drive element 234 normally retains the flexible arms 233 in engagement with the drive sleeve 231. However, before the reservoir 248 of damping fluid is exhausted, the flexible latch arms 233 linking the drive sleeve 231 with the first drive element 232 move sufficiently far forward relative to the second drive element 234 that the flange 270 is brought to register with a rebate 272 in the flexible arms 233, whereupon it ceases to be effective in retaining the flexible arms 233 in engagement with the drive sleeve 231. Now, the drive sleeve 231 moves the flexible latch arms 233 inwards from the position shown to a position at which they no longer couple the drive sleeve 231 to the first drive element 232, aided by the bevelled latching surfaces 274 on the flexible arms 233. Once this happens, the drive sleeve 231 acts no longer on the first drive element 232, allowing them to move relative to each other. At this point, of course, the syringe 214 is released, because the forces developed by the drive spring 230 are no longer being transmitted to the syringe 214, and the only force acting on the syringe will be the return force from the return spring 226. Thus, the syringe 214 now returns to its retracted position and the injection cycle is complete.

The invention claimed is:

1. An injection device comprising:
a housing adapted to receive a syringe having a discharge nozzle and having a boot that covers its discharge nozzle, so that the syringe is movable between a retracted position in which the discharge nozzle is contained within the housing and an extended position in which the discharge nozzle extends from the housing through an exit aperture, the housing including a return spring for biasing the syringe from its extended position to its retracted position;
a releasable locking mechanism that retains the syringe in its retracted position; and
a housing closure member that can occupy a first position, in which it locates on the housing and prevents the locking mechanism from being released, and a second position, in which it does not prevent the locking mechanism from being released, the first position of the housing closure member being one in which it engages the boot, so that movement of the housing closure member to its second position results in removal of the boot from the syringe;
a drive spring;
a drive that is acted upon by the drive spring and in turn acts upon the syringe to advance it from its retracted position to its extended position and discharge its contents through the discharge nozzle;
a release mechanism operable to release the releaseable locking mechanism, thus allowing the syringe to be advanced by the drive spring from its retracted position to its extended position, and in which the first position of the housing closure member is one in which it prevents the release mechanism from being operated;
a return mechanism, activated when the drive has reached a nominal return position, to release the syringe from the action of the drive spring, whereupon the return spring restores the syringe to its retracted position; and wherein
the releasable locking mechanism comprises a latch member that is located within the housing and is biased into a position in which the latch member engages a locking surface and the release mechanism acts to move the latch member from the position in which it engages the locking surface into a position in which the latch member no longer engages the locking surface.

2. An injection device according to claim 1 in which the first position of the housing closure member is one in which it closes the exit aperture to the discharge nozzle, and the second position is one in which it does not.

3. An injection device according to claim 2 in which the first position of the housing closure member is one in which it locates on the housing and the second position is one in which it does not.

4. An injection device according to claim 3 in which the housing closure member is a cap that locates onto the housing.

5. An injection device according to claim 1 in which the release mechanism is a primary member movable between locking and releasing positions and in which the first position of the housing closure member is one in which it covers the primary member.

6. An injection device according to claim 5 further comprising:
a trigger movable from a rest position, in which it causes the drive to be retained in a position corresponding to the retracted position of the syringe, to an operative position, in which it no longer causes the drive to be so retained, thus allowing it to be advanced by the drive spring and in turn to advance the syringe form its retracted position to its extended position and discharge its contents through the discharge nozzle; and an interlock member comprising the primary member, the interlock member being movable between a locking position, at which it prevents movement of the trigger from its rest position to its active position and the primary member projects from the exit aperture, and a releasing position, at which it allows movement of the trigger from its rest position to its active position and the primary member does not project from the exit aperture or projects from it to a lesser extent, the trigger thereafter being retained in its active position.

7. An injection device according to claim 6, in which the trigger comprises a locking member that, in the rest position of the trigger, engages a locking surface of the drive and, in the active position, does not.

8. An injection device according to claim 7 in which the trigger and another component of the device include a latching projection and a corresponding latching surface against which the latching projection latches when the trigger is in its active position.

9. An injection device according to claim 8 in which the latching projection is on the trigger.

10. An injection device according to claim 9 in which the said other component of the device is the interlock member.

11. An injection device according to claim 7 in which the trigger and the interlock member include a projection and an aperture, the projection being in register with the aperture when the interlock member is in its releasing position, but not otherwise, thus allowing the trigger to move from its rest position to its active position by movement of the projection into the aperture.

12. An injection device according to claim 11 in which the projection is on the trigger and the aperture is in the interlock member.

13. An injection device according to claim 5 in which the locking position of the primary member is one in which it projects from the exit aperture and the releasing position is one in which it does not project from the exit aperture or projects from it to a lesser extent.

14. An injection device according to claim 13 in which the primary member is a sleeve.

15. An injection device according to claim 14 in which the primary member includes a latch opening through which the latch member projects before it engages the locking surface, the primary member acting as a cam and the latch member as a cam follower, so that movement of the primary member from its locking position to its releasing position causes the latch member to disengage from the locking surface.

16. An injection device according to claim 15 in which the latch member includes a ramped surface against which a surface of the primary member acts to disengage it from the locking surface.

17. An injection device according to claim 1 further comprising:

a trigger movable from a rest position, in which it causes the drive to be retained in a position corresponding to the retracted position of the syringe, to an active position, in which it no longer causes the drive to be so retained, thus allowing it to be advanced by the drive spring and in turn to advance the syringe from its retracted position to its extended position and discharge its contents through the discharge nozzle; and an interlock member movable between a locking position, at which it prevents movement of the trigger from its rest position to its active position, and a releasing position, at which it allows movement of the trigger from its rest position to its active position, the trigger thereafter being retained in its active position.

\* \* \* \* \*